(12) United States Patent
Clark

(10) Patent No.: US 10,398,360 B1
(45) Date of Patent: Sep. 3, 2019

(54) METHOD TO ENHANCE AUDIO SIGNAL FROM AN AUDIO OUTPUT DEVICE

(71) Applicant: Mimi Hearing Technologies GmbH, Berlin (DE)

(72) Inventor: Nicholas R. Clark, Royston (GB)

(73) Assignee: Mimi Hearing Technologies GmbH (DE)

( * ) Notice: Subject to any disclaimer, the term of this patent is extended or adjusted under 35 U.S.C. 154(b) by 0 days.

(21) Appl. No.: 16/201,839

(22) Filed: Nov. 27, 2018

(30) Foreign Application Priority Data

Oct. 15, 2018 (EP) .................................... 18200368

(51) Int. Cl.
| | |
|---|---|
| *G10L 21/0232* | (2013.01) |
| *H04B 15/00* | (2006.01) |
| *H03G 5/00* | (2006.01) |
| *A61B 5/12* | (2006.01) |
| *H04R 25/00* | (2006.01) |

(52) U.S. Cl.
CPC ............. *A61B 5/123* (2013.01); *H03G 5/005* (2013.01); *H04R 25/55* (2013.01)

(58) Field of Classification Search
CPC ........ A61B 5/121; A61B 5/128; H04R 25/75; A61M 2021/0027
USPC ................................ 381/98, 103, 94.1–94.4
See application file for complete search history.

(56) References Cited

U.S. PATENT DOCUMENTS

2002/0150261 A1\* 10/2002 Moeller ............... G10K 11/175
  381/73.1
2004/0141624 A1\* 7/2004 Davis ..................... A61B 5/121
  381/73.1

\* cited by examiner

*Primary Examiner* — George C Monikang
(74) *Attorney, Agent, or Firm* — Polsinelli PC

(57) ABSTRACT

A method of enhancing an audio signal from an audio output device is provided. For a frequency band, a user masking contour curve covering at least a part of said frequency band is obtained, a target masking contour curve is derived from the user masking contour curve, and a multi-band digital compression system is parameterized based on the sound level of the target masking contour curve at a given frequency and the sound level of the user masking contour curve at the same given frequency. The obtained parameters are outputted to provide an enhanced audio signal.

28 Claims, 8 Drawing Sheets

METHOD TO ENHANCE AUDIO SIGNAL FROM AN AUDIO OUTPUT DEVICE

CROSS-REFERENCE TO RELATED APPLICATIONS

This Non-Provisional application claims priority to European Application No. 18200368.1, filed Oct. 15, 2018, and which is entirely incorporated by reference herein.

FIELD OF THE INVENTION

The present invention relates to a method to enhance an audio signal from an audio output device from a user's hearing profile to provide an enhanced hearing experience to the user.

BACKGROUND

The pure tone audiogram is an individual representation of the minimum audible stimulus threshold. It represents the minimum sound intensity at a particular frequency that a person is able to detect. As such, the audiogram is easy to understand, and recognised as the global standard for diagnosing hearing loss.

Traditional sound personalization methods often rely on linear filtering techniques such as equalization (EQ) that apply compensatory frequency gain according to a user's hearing profile. For example, U.S. Pat. No. 9,748,914B2 discloses a method and apparatus for processing an audio signal, based on boosting or attenuating an input signal at one or more frequencies. Likewise, U.S. Pat. No. 9,680,438B2 describes a method for modifying audio signals in accordance with hearing capabilities of an individual who is listening to audio signals played by a music player. However, the entire application also refers to equalizing techniques. This form of intervention is only applicable to conductive hearing loss, a condition caused by poor energy transfer to the inner ear, specifically deficient conduction of sound energy anywhere along the route through the outer ear, tympanic membrane (eardrum), or middle ear (ossicles). This type of hearing loss is relatively rare and more readily treatable compared to sensorineural hearing loss, which originates in the inner ear. In addition, the human auditory system has been proven to be highly non-linear, and hearing impairment cannot be modelled as a filter as such.

Non-linear amplification is a form of dynamics compression, present i.e. in conventional hearing aids. Conventional hearing aids are designed for use in real world situations where a wide dynamic range of sounds are relevant to the user, i.e. the user wants to make sense of sonic information such as a loud-voiced person speaking in front of them, while at the same time being able to detect the faint sound of a car approaching them from distance while walking down the street. For this reason, the primary function of a hearing aid is to employ wide dynamic range compression (WDC) where the faintest sounds are amplified considerably, but where high-intensity sounds are not. Audio content consumed on mobile devices has very different signal statistics to the sounds that someone will encounter in their daily life, and so a different processing strategy is required to provide the listener with a beneficial sound personalization experience.

The theoretical maximum dynamic range 16-bit of CD-quality audio is approximately 96 dB, designed to cover most of the perceptually relevant intensity range of healthy human hearing. However, this range is rarely achieved in reality due to inefficiencies in the digital-to-analogue conversion process. Trends in techniques employed in sound recording, production, and distribution processes mean that in actuality, almost all digital content consumed by the end user has significantly less dynamic range.

For example, orchestral music, while often cited for its relatively wide dynamic range, typically contains all sonic content within just 40 dB, while rock music is within 20 dB across most of the frequency spectrum. Speech content consumed on mobile platforms, such as voice communications, podcasts, radio is similarly dynamic-range-compressed.

Kirchberger and Russell (2016) tested the impact of conventional hearing aid processing on the perceived quality of such audio content, and concluded that it had a negative effect on the perceived quality of the experience by hearing impaired listeners. The result is in line with expectations, because the signal statistics of the types of audio content likely to be consumed on mobile devices are so different from those designed for a conventional hearing aid.

Given that an EQ is not suitable for the task of sound personalisation based on the hearing profile of an individual, and given that conventional hearing aid processing provides no benefit to hearing impaired listeners when consuming recorded audio content, there is a clear requirement for a novel, targeted class of audio processing. Accordingly, it is the object of the present invention to provide a better quality of experience to (hearing impaired) users when consuming recorded audio content.

SUMMARY OF THE INVENTION

The present invention seeks to address the aforementioned problems. The features according to the invention are specified within the independent claims, advantageous implementations of which will be shown in the dependent claims. The features of the claims can be combined in any technically meaningful way, and the explanations from the following specification as well as features from the figures which show additional embodiments of the invention can be considered.

Methods for the enhancements of audio content, such as recorded audio content, aim at transforming said audio content so that it is perceived as similar as possible to how the content would be perceived by a user with good hearing abilities. By averaging results of the hearing abilities of people having good or normal hearing abilities, i.e. who can hear sounds softer than 20 dB, a profile corresponding to a "reference hearing" profile (e.g., a reference masking contour curve) could be defined.

Typically, "user with mild hearing loss" refers to a user which cannot hear sounds softer than 20 to 40 dB, "user with moderate hearing loss" refers to a user which cannot hear sounds softer than 40 to 70 dB, "user with severe hearing loss" refers to a user which cannot hear sounds softer than 70 to 90 dB, and "user with profound hearing loss" refers to a user which cannot hear sounds softer than 90 to 120 dB.

The audio signal may therefore be customized so that it fits the specific hearing profile of a user. Since every user has a unique hearing profile, i.e. there is a different way of perceiving sound signals played at different frequencies.

In the context of the present invention, a hearing profile may refer to information derived from a user's hearing abilities. A user hearing profile may be derived from a user's demographic data such as, but not limited to: age, sex, ethnicity, race, country of residence, average exposure to noise. A user's hearing profile may also be derived from a hearing test, including, but not limited to, pure-tone-threshold hearing tests, which determine the Minimal Audible Threshold (MAT) of a user, represented on an audiogram, and supra-threshold hearing tests.

An aspect of the invention relates to a method of enhancing an audio signal from an audio output device, the method comprising, for a frequency band: i) obtaining a user masking contour curve, covering at least a part of said frequency band, ii) deriving a target masking contour curve from the user masking contour curve, iii) parameterizing a digital compression system based on the sound level of the target masking contour curve at a given frequency and the sound level of the user masking contour curve at the same given frequency, and iv) outputting the parameters of the digital compression system. The method may further comprise v) processing an output audio signal to provide an enhanced audio signal.

Thus, in the above aspect, parameters for setting up a multi-band compressor may be derived from comparing a target masking contour curve with a user's masking contour curve (user masking contour curve).

In an embodiment of the present invention, the user's hearing profile (e.g., user masking contour curve (MCC)), for example obtained from a hearing test, may comprise data for the user's left ear and the user's right ear. Indeed, both ears may have a different profile or hearing ability, i.e. one ear may be more damaged or healthy than the other ear. Notably, methods according to aspects and embodiments of the invention may be performed for each ear separately.

In an embodiment of the present invention, the user's hearing profile (e.g., user MCC) may be derived from a supra-threshold hearing test. Supra-threshold hearing tests have the advantage to provide richer information about the state of a user's hearing, and of the function of different components within the ear. Data from supra-threshold tests can be used to more effectively set up a hearing instrument or personalised audio experience than the MAT alone.

Supra-threshold tests may include, but are not limited to, tests that estimate spectral resolution, i.e. estimation of psychophysical tuning curves, or tests that estimate temporal resolution, either on the macro scale using tasks such as such as gap detection, or on the micro scale using tests that estimate the usefulness of temporal fine structure cues to the individual. Psychoacoustic tuning curves rely on a masking paradigm, whereas some other supra-threshold tests, such as a Temporal Fine Structure (TFS) test or a gap detection test, do not rely on masking paradigms. Masking may be defined as the rendering of one sound inaudible by the presence of another sound. For example, a signal tone may be masked by a masker noise. Simultaneous masking occurs when a sound is made inaudible by a masker presented simultaneously with the signal. Temporal, or non-simultaneous masking occurs when a masker gives rise to a masking effect on a signal that occurs before or after the masker.

The term "masking contour curve" may be defined herein as the result of any test involving a masking paradigm. A masking contour curve is typically a function of a measure of the effectiveness of a masker in terms of intensity required to mask a signal, or signal tone, versus a measure of the frequency difference between the masker and the signal. A masker contour curve can be said to be an estimate of the user's cochlear spectral resolution. It relies on a behavioural test of cochlear tuning rather than a direct measure of cochlear activity using neural probes. This has the advantage to provide an easy, pain-free and non-cumbersome way of estimating a user's cochlear resolution. A masking contour curve may also be referred to as a psychophysical or psychoacoustic tuning curve (PTC). Such a curve may be derived from one of a number of types of tests: for example, it may be the results of Brian Moore's fast PTC, or Patterson's notched noise method.

In an embodiment of the present invention, the masker is a noise sweeping (by varying in frequency and in level) over a constant signal tone. The center frequency is the frequency of the signal tone. The signal tone may be a pure tone, i.e. a tone with a sinusoidal waveform.

In another possible configuration, the signal sweeps (by varying in frequency and in level) over a constant masker noise. The center frequency in this case may be defined as an average frequency of the constant masker noise.

Both configurations give similar results. The process in which a noise sweeps over a constant signal tone results in a V-shaped masking contour curve. The process in which a signal sweeps over a constant noise masker results in a reverse V shape. Each configuration can be said to be the 180 degrees center rotation of the other one.

In another embodiment of the present invention, masking contour curve tests may be performed around signal tones or noise having different, fixed center frequencies. These different center frequencies may be standard frequencies such as 500 Hz, 1 kHz, 2 kHz, 3 kHz, 4 kHz, 8 kHz, 16 kHz.

The masking contour curve tests may be performed at frequencies belonging to the human auditory spectrum, typically ranging from 16 Hz to 20 000 Hz. The human auditory spectrum, or part of it, may be divided into frequency bands, each corresponding to a range of frequency. The division of the auditory spectrum into frequency bands may be based on critical bands, such as the critical bands defined by Harvey Fletcher, for example. Other ways to define the frequency bands are feasible as well. For example, the frequency bands may also be set in an arbitrary way.

The masking contour curve typically extend on several frequency bands. Typically, a masking contour curve extends on at least three frequency bands. Masking contour curve tests performed at different signal tones may overlap. They may extend over a large portion of the auditory spectrum, if not covering it entirely.

A (user) masking contour curve may be the result of a psychoacoustic tuning curve test.

In an embodiment of the present invention, obtaining a (user) masking contour curve may involve selecting a masking contour curve from a prestored set of masking contour curves. The prestored set may be specific to the user in question. A (user) masking contour curve may also be selected from a database of hearing profiles comprising masking contour curves (in this case, the prestored set would not be specific to the user). The selection may be based on demographic data, such as the age or year of birth of the user.

In the context of the present invention, both a "reference" and a "target" masking contour curves may typically be "sharper" than the masking contour curves of users with mild, moderate, severe or profound hearing loss, who typically obtain broader curves.

The broadness of a PTC may be quantified by determining a width (along frequency) $w_{lvl}$ at a certain sound level (in dB) above the tip level (the tip level corresponding to the sound level at the minimum value of the PTC). Typically, the $w_{10}$, determining the broadness of a PTC curve at 10 dB above the tip level, may be used used. However, any other suitable measure of broadness may be used as well. Quality factors may be calculated at different sound levels relative to the tip level, given by:

$$Q_{lvl} = \frac{F_{tip}}{w_{lvl}}$$

With $Q_{lvl}$ representing the quality factor at the level (M) in dBs relative to the PTC tip level, $F_{tip}$ the tip frequency, and w the broadness of the curve at a level (M) above the tip level. The $Q_{10}$ is typically a quality factor at 10 dB above the tip level. In general, the quality factor may be determined as a ratio between the tip frequency of the PTC and a measure of width (or broadness) of the PTC.

In one embodiment of the present invention, a masking contour curve may be derived from information on a user's hearing ability, such as a user's demographic data, for example the age, sex, ethnicity and/or country of residence. By looking at ISO standards for age and sex in MAT measurements, clear correlations may be observed, making it possible to derive an estimate MAT from a user's demographic information.

Furthermore, there is a correlation between masking contour curves and the MAT. It is possible to derive at least one absolute pure tone threshold from the general shape of a masking contour curve, and vice versa. Therefore, it is possible to predict a user's masking contour curve starting from its demographic information and/or its MAT. The estimation of a pure tone threshold from the shape of a masking contour curve is described in detail in European patent application EP 3 311 741 A1.

A "target" masking contour curve may be determined based on a reference masking contour curve and the user masking contour curve. In addition, the target masking contour curve may be determined further based on the center frequency of the user masking contour curve (e.g., the tip frequency) and/or a confidence parameter. In an embodiment of the present invention, the reference masking contour curve may be constant (e.g., referring to average results of people having good or normal hearing abilities).

For example, the target masking contour curve may be interpolated using the reference masking contour curve and the user masking contour curve. In other words, the target masking contour curve may be obtained by interpolation between the reference masking contour curve and the user masking contour curve. A target masking contour curve may be understood in this context as a masking contour curve which already reflects an improved hearing ability (e.g., compared to the user masking contour curve). In an embodiment of the present invention, the target masking contour curve may have a course of function between the user masking contour curve and the reference masking contour curve, i.e., that is not below the user masking contour curve and not above the reference contour curve.

In some embodiments of the present invention, the target masking contour curve may be derived from a function and may be dependent on at least one or more of the following parameters: the reference masking contour curve and the user masking contour curve, the center frequency of the user masking contour curve, and the confidence parameter.

The confidence parameter of the user masking contour curve may be indicative of a reliability of the user masking contour curve, e.g., the likelihood that the user masking contour curve faithfully represents the user's hearing abilities. It may be derived for example from metrics such as the number of reversals in a psychometric test, the consistency of someone's response, ambient sound monitoring or monitoring of the background noise, and/or similarity to previous results. The confidence parameter may be positively correlated to a coefficient of sharpening (e.g., a linear interpolation coefficient) that is indicative of how close the target masking contour curve is to the reference masking contour curve. The higher the confidence value, the closer the target masking contour curve may be to the reference masking contour curve.

The phrase "optimization of a masking contour curve" may be understood as the obtaining of a masking contour curve that is sharper, and thus has a higher $Q_{lvl}$ compared to the masking contour curve of the user. A sharper masking contour curve typically reflects an enhanced perception of the audio content by the user, which may for example be highlighted by taking a supra-threshold test and comparing the results to the user's previous results, by asking the user if he notices an improvement, or by measuring the quality factor $Q_{lvl}$.

In another embodiment of the present invention, at least one multi-band processor may be parameterized according to the user's hearing profile and the associated target masking contour curve to which the user's masking contour curve is compared.

Multi-band processors process sound by splitting the audio signal into a plurality of frequency band signals through spectral decomposition. This splitting into multiple frequency bands may be achieved by applying the audio signal to a plurality of parallel bandpass filters, one for each frequency band. The phrase "bandpass filter", as used herein, is defined as a device that passes frequencies within a certain range and attenuates frequencies outside that range. Multi-band processors therefore have the advantage to process sound in a dynamic way.

For a multi-band processor, the method according to the above aspects and embodiments may be performed for each of a plurality of frequency bands.

In an embodiment of the present invention, the multi-band processor may be a multi-band compression system (compressor), in which the processor is a dynamic range compressor (DRC). In the context of the present invention, each frequency band associated to a processor such as a DRC may also be referred to as a channel.

A multi-band compressor has the further advantage of giving the ability of setting up parameters for each band of frequencies or channel separately. In an embodiment of the present invention, for each channel, at least two parameters of the multi-band processor are determined or altered. In a preferred embodiment of the present invention, the at least two parameters that are determined or altered comprise the threshold and ratio values of each band DRC. Here, the threshold defines that signal level above which gain expansion or gain reduction is applied to the audio signal, and the ratio defines the actual gain that is applied for signal levels above the threshold.

In an embodiment of the present invention, a set of parameters (e.g., including the threshold and the ratio) may be set for every frequency band or channel in a group of frequency bands or channels (e.g., for every frequency band of the human auditory spectrum).

In another embodiment of the present invention, further parameters may be determined or modified. These parameters may comprise, but are not limited to delay between envelope detection and gain application, integration time constants used in the sound energy envelope extraction phase of dynamic range compression, and static gain.

In the context of the present invention, the "threshold" parameter is understood as the level (in dB Full Scale, dB FS) above which compression is applied in an instantaneous compressor (i.e. there is no integration of envelope energy required to calculate gain or attenuation, and thus an instantaneous compressor is the most basic form of dynamics processor).

In the context of the present invention, the "ratio" parameter is understood as the gain (if the ratio is positive), or attenuation (if the ratio is a fraction in the range between zero and one) per decibel for a signal level exceeding the compression threshold. In an embodiment of the present invention, the ratio is a fraction comprised between zero and one. Even more preferably, the ratio is comprised between 0.2 and 1. In an embodiment of the present invention, the parameterizing is specific to each channel. The advantage allows adapting the sound level, which is an objective characteristic, to the sound level perception, which is subjective, across frequencies.

In an embodiment of the present invention, one way of setting up the ratio and threshold parameters in a multi-band compression system is to make the threshold and ratio satisfy the condition that the signal-to-noise ratio (SNR) of the user masking contour curve at a given frequency is made to equal the SNR of the target masking contour curve at the same given frequency by application of the compression system. The SNR is defined as the sound level of the signal tone compared to the sound level of the masker noise at a given frequency. The sound level (dB) of the target masking curve at a given frequency corresponds to an input sound level entering the compression system. The objective is that the sound level outputted by the compression system will match the user masking contour curve at the same given frequency. This allows to derive the threshold (which has to be below the input sound level, if not, there is no change as below the threshold of the compressor, the system is linear) and the ratio parameters in the multi-band compression system. In an embodiment of the present invention, one of the parameters ratio and threshold is initially set, and the other parameter is derived from it. For example, the one parameter may be set to a default value. As another example, the one parameter may be arbitrarily set. As a further example, the previous steps are reiterated one or more times at other given frequencies of the frequency band, and combining the results allow to derive a set of parameters.

In a further embodiment of the present invention, the obtained setup of the parameters is transferred to a processor.

In a further embodiment of the present invention, the processor subsequently processes the audio signal to provide an enhanced audio signal.

In an embodiment of the present invention, the output audio device from which the enhanced audio signal is outputted may be a mobile phone, a smartphone, a tablet, a computer, a television, a hearable (such as a headphone or an earpiece), a smart speaker, a hearing aid, a speaker system, a home entertainment system, a car entertainment system, an in-flight entertainment system, or any device outputting audio signals (for example, but not limited to, for entertainment purposes).

In the context of the present invention, the term "enhanced" is understood as providing an objectively and/or subjectively improved sound quality to the user.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understand that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

Figure 1:
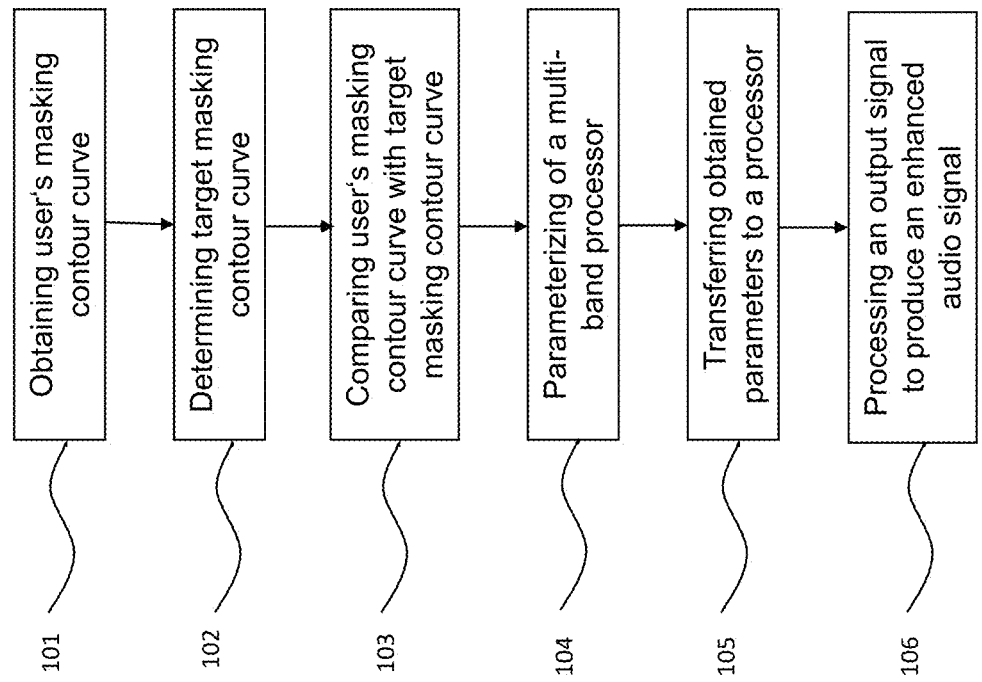
FIG. 1 is a flow diagram exemplifying a method carried out in accordance with an embodiment of the present invention.

FIG. 1 is a flow diagram illustrating a non-limiting example of a method carried out in accordance with an embodiment of the present invention.

The process of FIG. 1 may be performed in each one of a plurality of frequency bands.

In step 101, the masking contour curve of a user is obtained. The phrase "masking contour curve" as used herein refers to a result obtainable from a psychoacoustic tuning curve test. The test may be performed once or several times, and can be performed at different center frequencies, for example at 500 Hz, 1000 Hz, 2000 Hz, 3000 Hz, 4000 Hz, 8000 Hz, 16000 Hz etc. As the case may be, the masking contour curve can be obtained directly from taking a test that can be performed on a consumer audio device, such as a smartphone of a computer, or derived from information on the user, such as a user's demographic data (age, sex, ethnicity, country of residence, average exposure to noise, . . . ), or a hearing test, such as pure-tone threshold test determining the minimal audible threshold of a user, or other supra-threshold hearing tests.

For each frequency band, the user masking contour curve can be selected from a plurality of prestored masking contour curves that may have different center frequencies. These masking contour curves may have been generated specifically for the user in question, for example during a hearing test. Alternatively, appropriate selection may be made from a database that stores masking contour curves of a plurality of test subjects, wherein the selection is mad in accordance with the user's demographic data.

A masking contour curve may be the result of a psychoacoustic tuning curve test performed with a certain signal tone frequency. The masking contour curve typically extend on several frequency bands, typically on at least three frequency bands. Performing a psychoacoustic tuning curve test at different center frequencies, for example at 500 Hz, 1000 Hz, 2000 Hz, 4000 Hz and 8000 Hz, allows to cover most of the auditory spectrum. The masking contour curves may overlap. Ideally, a frequency band should comprise at least a part of a masking contour curve.

The frequency band for which a set of parameters should be obtained (i.e., the user masking contour curve obtained at step 101) preferably does not comprise the center frequency of the masking contour curve. Preferable, the frequency band for which a set of parameters should be obtained is adjacent to the frequency band comprising the center frequency. Thus, in some embodiments the user masking contour curve is selected such that its center frequency is not in the frequency band in question, but the user masking contour curve extends into, or through, the frequency band in question. Preferably, the user masking contour curve extends through several frequency bands, typically at least three frequency bands.

Step 102 involves determining a target masking contour curve for the user. One way of determining a target masking contour curve is to derive it from the user's masking contour curve and from a standard and constant sharp masking contour curve corresponding to a (reference) user with good hearing ability, which we call reference masking contour curve here, at a certain center frequency. Therein, the reference masking contour curve and the user masking contour curve should have (substantially) the same center frequency. The target masking contour curve is interpolated from (e.g., between) the user masking contour curve and the reference masking contour curve, such that the target masking contour curve always runs between the user and reference masking contour curves and respective lower and upper limits. In extreme cases, the target masking contour curve may correspond to the reference masking contour curve. Further parameters such as the center frequency and/or a confidence factor may also influence the interpolation that leads to the target masking contour curve. Likewise, the target masking contour curve corresponding to a user masking contour curve may extend on several frequency bands, typically on at least three frequency bands.

In step 103, the user's masking contour curve is compared with the target masking contour curve at a given frequency within a given channel or frequency band. A channel is herein understood to be equivalent to a frequency band. The given frequency is preferably not in the same frequency band or channel as the center frequency of the masking contour curve. In one embodiment of the present invention this step comprises the determination of a signal-to-noise ratio for the user masking contour curve and the target masking contour curve a this given frequency. The signal-to-noise ratio is herein defined as the level of the signal tone compared to the level of the masker tone.

Step 104 involves in determining at least two parameters of a compression system (e.g., for the present frequency band in a multi-band compression system), the threshold and the ratio of a compression system for the frequency band. At least two parameters, the threshold and the ratio of a compression system for the frequency band can be derived from the signal-to-noise ratio (SNR). The signal-to-noise ratio of the target masking contour curve at a given frequency should be decreased by application of the compression system to become as low as the signal-to-noise ratio of the user masking contour curve at the same given frequency.

Effectively, when the system operates, it means that from a user standpoint, the signal-to-noise ratio of the user masking contour curve at a given frequency should be increased by application of the compression system to become as high as the signal-to-noise ratio of the target masking contour curve at the same given frequency.

In step 105, the parameters obtained for the frequency band are transferred to a processor.

Steps 103 to 105 may be performed for each one of a plurality of frequency bands.

In step 106, the processor processes the audio signal (output from the audio output device) in order to produce an enhanced audio signal. The processing can be performed in each of the frequency bands, using respective parameters. The processing may occur on a dynamic range compressor (DRC). As the case may be, the audio signal is outputted on a mobile phone, computer, television, hearing aid, headphones and/or speaker system.

Figure 2:
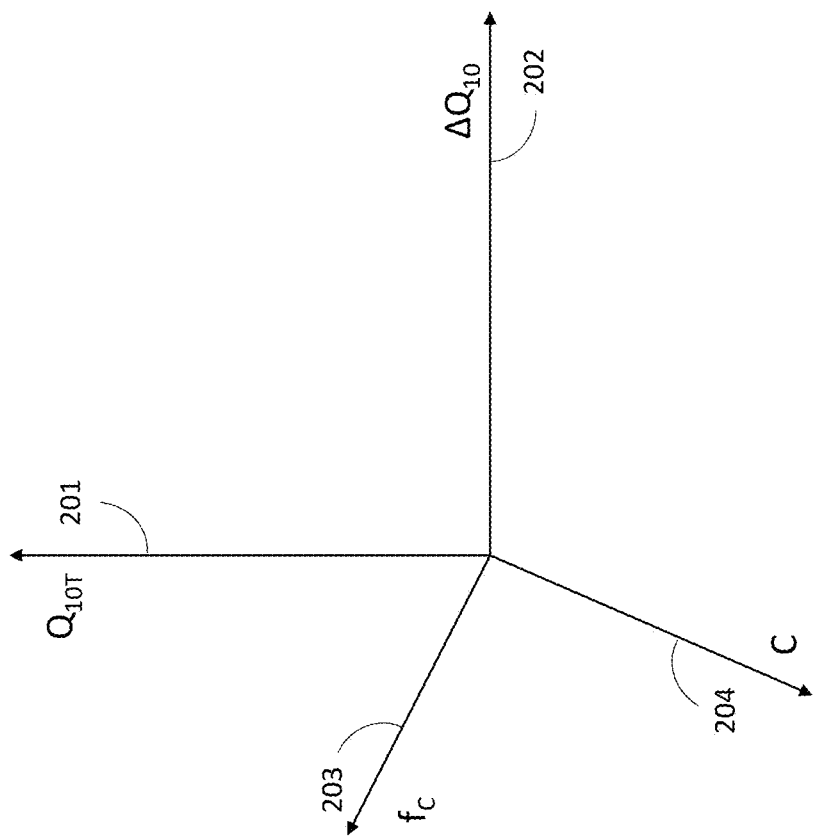
FIG. 2 describes an example of a function to determine a target curve.

FIG. 2 shows the variables that may be used in determining the target masking contour curve. The target curve is defined by its quality factor $Q_{lvl\ T}$, (e.g., quality factor $Q_{10T}$ 201 in the example of FIG. 2) and depends at least on $\Delta Q_{lvl}$ (e.g., $\Delta Q_{10}$ 202 in the example of FIG. 2), i.e., the difference between the quality factor of the reference masking contour curve at a predefined level and the quality factor of the user masking contour curve at the predefined level. $\Delta Q_{10}$ 202 in FIG. 2 is defined as the difference between the quality factor of the reference masking contour curve $Q_{10R}$ and the quality factor of the user's masking contour curve $Q_{10U}$:

$$\Delta Q_{10} = Q_{10R} - Q_{10U}$$

The target masking contour curve may be based on $\Delta Q_{lvl}$. The target masking contour curve may also further depend on the center frequency $f_c$ 203. The target masking contour curve may further be based on a confidence parameter C 204. The confidence parameter (of the user masking contour curve) may be indicative of a reliability of the user masking contour curve, e.g., the likelihood that the user masking contour curve faithfully represents the user's hearing abilities. It may be derived for example from metrics such as the number of reversals in a psychometric test, the consistency of someone's response, ambient sound monitoring or monitoring of the background noise, and/or similarity to previous results.

Using the target curve is preferred over directly using the reference curve because fitting an audio signal to a reference curve is not necessarily optimal. Depending on the initial hearing ability of the user, fitting the processing according to a reference curve may cause an excess of processing to spoil the quality of the signal. The objective is to process the signal in order to obtain a good balance between an objective benefit and a good sound quality.

The target masking contour curve may be obtained (e.g., at step 102) by interpolating between the user masking contour curve and the reference masking contour curve. Interpolation may involve an interpolation factor $\Phi$. The interpolation factor may be a function of the confidence value (confidence parameter) C and/or the center frequency $f_c$. The interpolation factor may take values between 0 and 1, wherein a value of 0 indicates that the target masking contour curve corresponds to the user masking contour curve and a value of 1 indicates that the target masking contour curve corresponds to the reference masking contour curve. The interpolation factor may be positively correlated with the confidence value.

In some embodiments, the obtaining of a target masking contour curve may be exemplified as follows at—as a non-limiting example—a level of 10 dB:

$$Q_{10T} = Q_{10U} + (Q_{10R} - Q_{10U}) \times \Phi$$

Or $Q_{10T} = Q_{10U} + (\Delta Q_{10} \times \Phi)$ where Φ is a function of the center frequency $f_c$ and the confidence parameter C.

Figure 3:
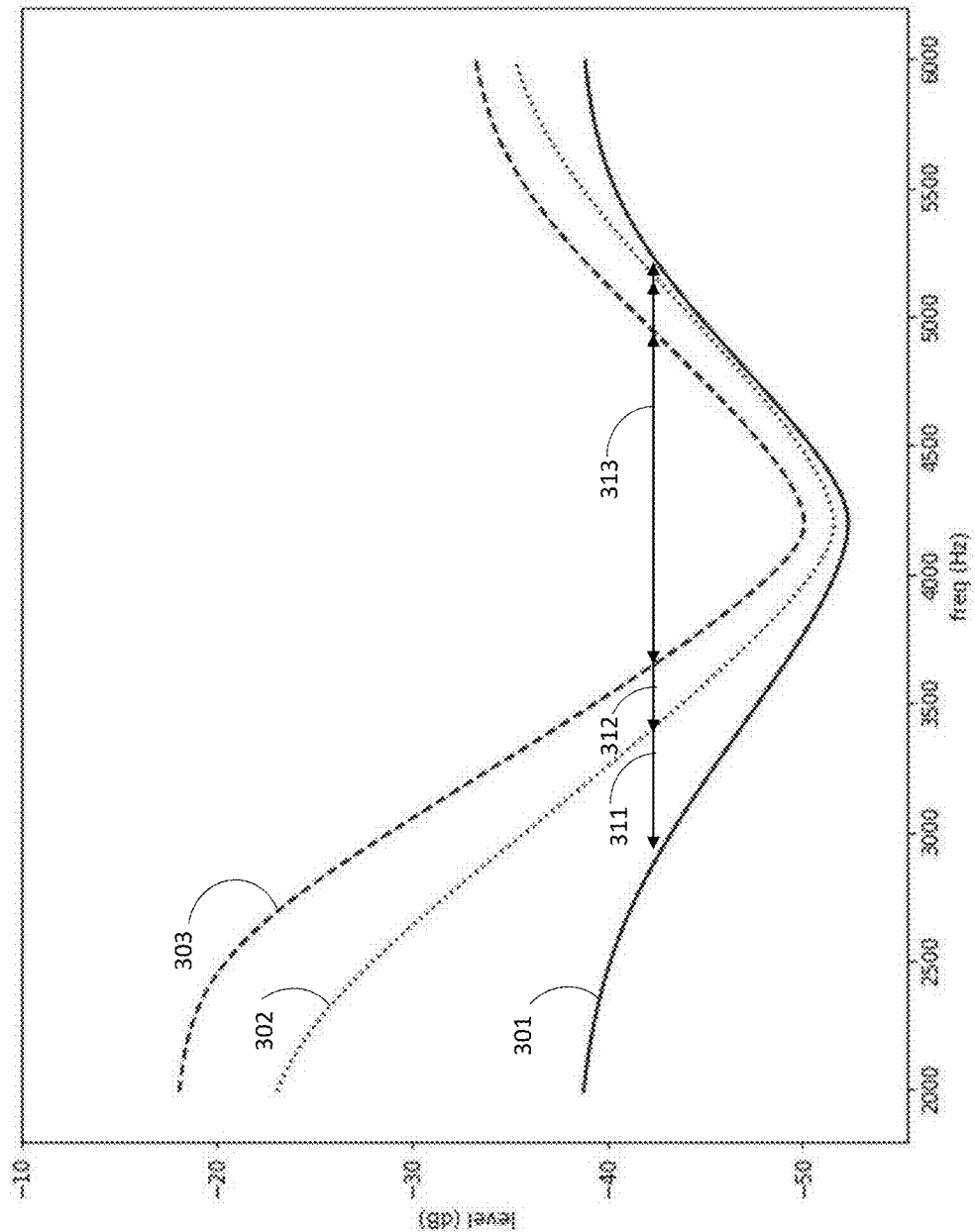
FIG. 3 illustrates examples of a "broad" and a "sharp" psychoacoustic tuning curve using the broadness at 10 dB above tip level, $w_{10}$.

The optimization of a user's masking contour curve 301 into a target masking contour curve 302 is illustrated on FIG. 3. In this example, the user masking contour curve 301 was obtained from a PTC test of a user with moderate hearing loss, which means the user is not able to hear sounds softer than 40 to 70 dB. The target masking contour curve 302 was mapped by following the method described in FIG. 2, using a standard reference masking contour curve 303 and the user masking contour curve 301. The target masking contour curve may typically be described as "sharper" or "less broad" than the user masking contour curves 301. The broadness of a masking contour curve is quantified by a $w_{lvl}$ at a certain level above the tip level (the tip level corresponding to the sound level at the minimum value of the PTC), for example $w_{10}$ corresponds to the broadness of the curve at 10 dB above tip level. The $w_{10U}$ 311 for the masking contour curve of the user is significantly higher than the $w_{10T}$ 312 corresponding to the target masking contour curve and $w_{10R}$ 313 corresponding to the reference masking contour curve. The higher the difference between the two $w_{10}$ 311 and 312, the more efficient the optimization of the masking contour curve.

Figure 4:
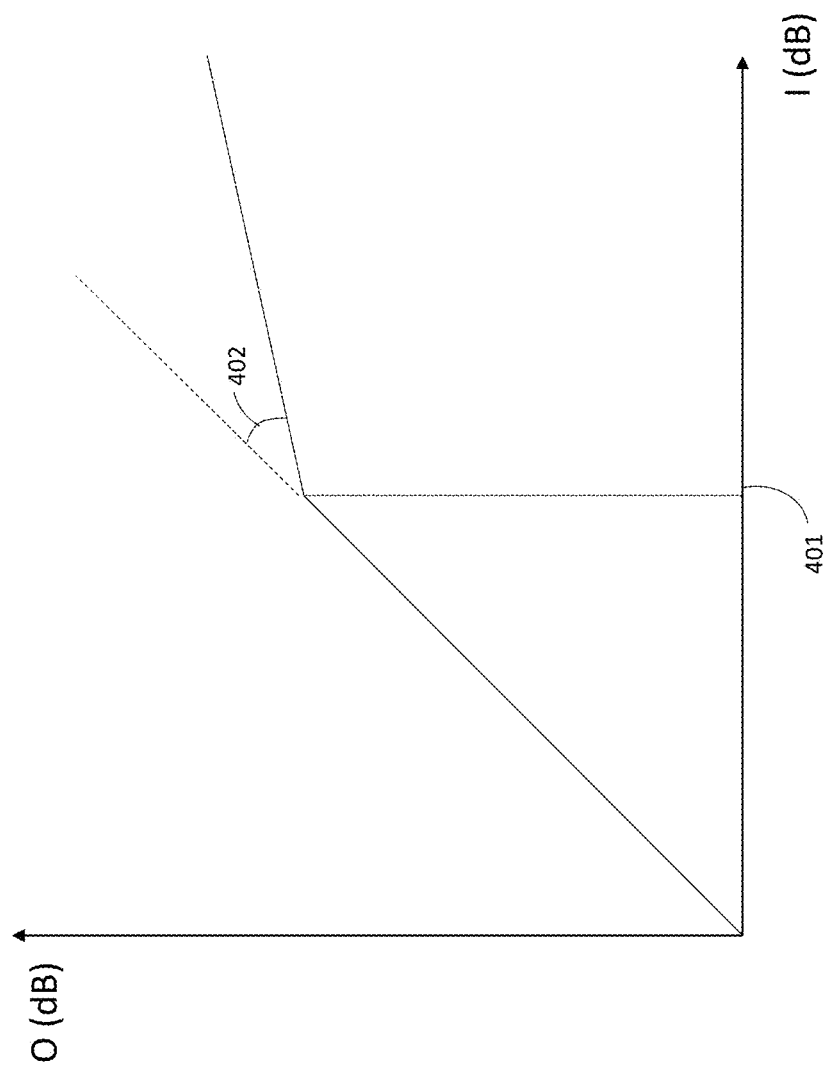
FIG. 4 illustrates examples of the threshold and ratio parameters of a multi-band compressor on an input/output graph.

The setting of the at least one multi-band compressor (e.g., at step 104) comprises determining or altering at least two parameters, as illustrated on FIG. 4 on an input-output graph showing the input level I versus the output level O of a sound signal, in decibels relative to full scale (dB FS): the threshold 401 and the ratio 402. Below the threshold, the relationship between the input level and the output level is linear. The threshold 401 is the input level above which compression is applied in an instantaneous compressor, and the ratio 402 is defined as the attenuation rate at which compression is applied in a compression system above the threshold 401.

Figure 5:
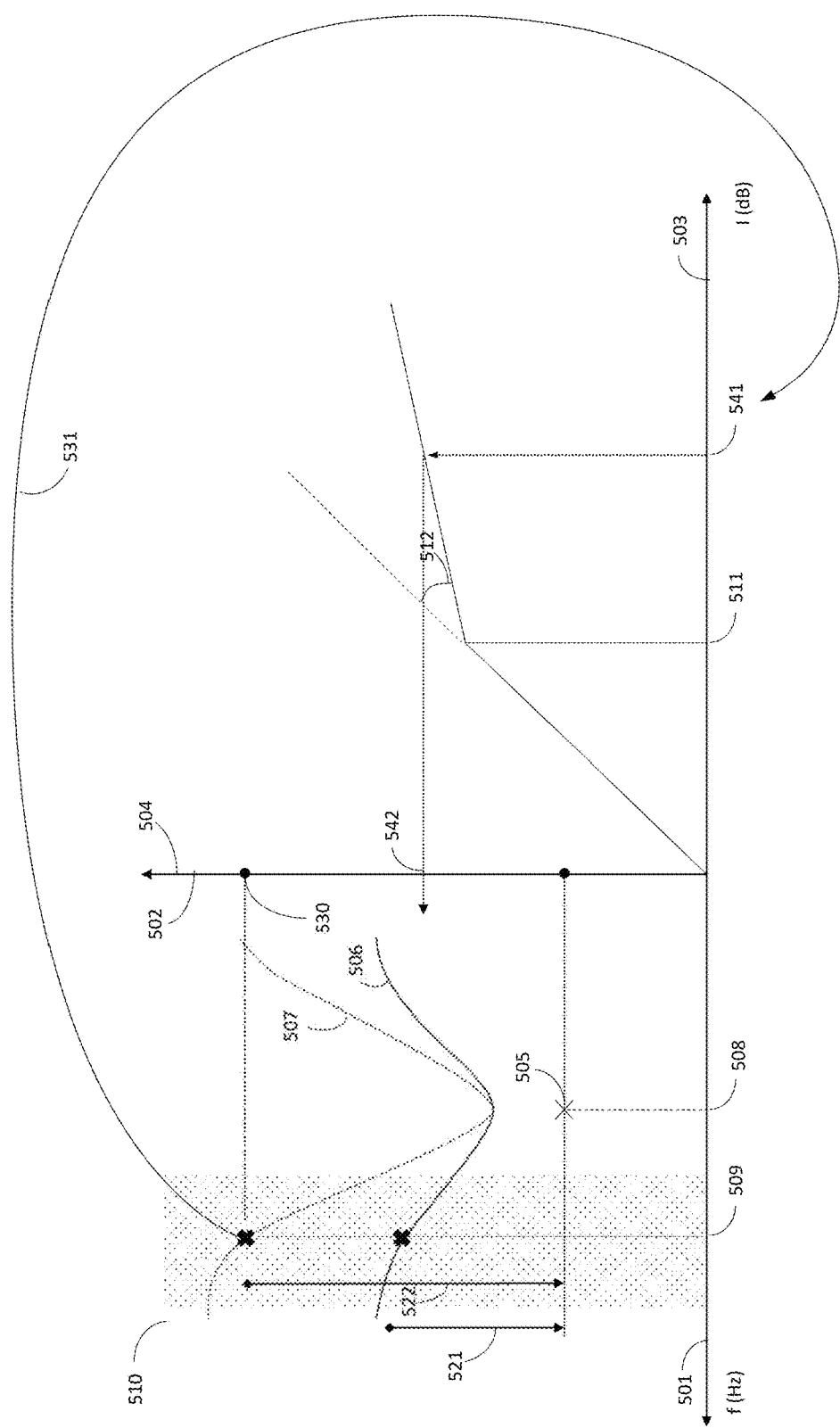
FIG. 5 illustrates an example of how to derive the threshold and ratio parameters.

FIG. 5 gives one way of setting up the ratio and threshold parameters for a channel (or frequency band) in a multi-band compression system (e.g., at step 104). FIG. 5 combines the visualization of the user masking contour curve 506 and target masking contour curve 507 of a constant tone or noise 505 at a center frequency 508 (x-axis 501 being frequency, y-axis 502 being the sound level in dB SPL or HL) and an input/output graph showing the input level 503 versus the output level 504 of a sound signal, in decibels relative to full scale (dB FS).

In the context of the present invention, the frequency band for which the set of parameters should be obtained is selected, and the method of FIG. 1 is performed for that frequency band. As noted above, the masking contour curves(s) are preferably selected such that their center frequency is in a frequency band adjacent to the frequency band in question.

In the context of the present invention, a masking contour curve may be obtained by a psychoacoustic test. For example, a psychoacoustic test can be conducted by masking of a constant tone or noise 505 by a masker noise, to thereby obtain a user masking contour curve 506. At least a part of a user masking contour curve should be in the frequency band 510 for which the set of parameters should be obtained. A target masking contour curve 507 is interpolated from at least the user masking contour curve and a reference masking contour curve.

The given frequency 509 is then chosen within the frequency band. It may be chosen arbitrarily, at a certain distance from the center frequency 508 of the constant tone or noise (which is preferably in the adjacent frequency band or another nearby frequency band). In any case, it is preferred that the given frequency 509 is in another frequency band 510 than the center frequency 508, as noted above. The corresponding sound levels of the user and target masking contour curves are determined at this given frequency 509. The value of these sound levels may be determined graphically on the y-axis 502.

The threshold 511 and ratio 512 must satisfy the condition that the signal-to-noise ratio 521 (SNR) of the user masking contour curve at a given frequency 509 is made to match the SNR 522 of the target masking contour curve at the same given frequency 509 by applying the compression system. The SNR is herein defined as the level of the signal tone relative to the level of the masker noise. The broader the curve will be, the greater the SNR.

Typically, in determining the respective masking contour curves, the sound level of the signal tone does not vary, and the noise level varies (noise is sweeping in frequency and level over a constant tone). In this case, the higher the noise level, the smaller the SNR will be (and the lower the noise level (situation of a broad PTC), the higher the SNR will be. The inverse configuration in which the noise level is fixed, and the signal tone varies is also a possible configuration. In this case, the masking contour curves should be rotated 180° around a center point.

The sound level 530 in dB of the target masking contour curve at a given frequency 509 corresponds (see bent arrow 531 in FIG. 5) to an input sound level 541 entering the compression system. The objective is that the sound level 542 outputted by the compression system will match the user masking contour curve 506 at the same given frequency 509, i.e., that his sound level 542 is substantially equal to the sound level in dB of the user masking contour curve at the given frequency 509. This condition allows to derive the threshold 511 (which has to be below the input sound level, if not, there is no change as below the threshold of the compressor, the system is linear) and the ratio 512.

The right panel in FIG. 5 (see the contiguous graph) illustrates a broken stick DRC (or bent knee DRC), with a threshold 511 and a ratio 512 as parameters that need to be determined. An input sound signal having a sound level 530/541 at a given frequency 509 enters the compression system. The sound signal should be processed by the DRC in such a way that the outputted sound level is the sound level of the user masking contour curve 506 at the given frequency 509. The threshold 511 should not exceed the input sound level 541, otherwise compression will not occur. Multiple sets of threshold and ratio parameters are possible. Preferred sets can be selected depending on a fitting algorithm and/or objective fitting data that have proven to show the most benefit in terms of sound quality. For example, either one of the threshold 511 and ratio 512 may be chosen to have a default value, and the respective other one of the parameters can then be determined by imposing the above-described condition. Another way of selecting a preferred set, is to repeat steps 103 and 104 (see FIG. 1) at one or more other given frequencies in the channel or frequency band. Having two or more sets of values of outputted sound level for an inputted sound level may allow to determine a set of parameters (threshold and ratio) with more accuracy.

Preferably, the ratio is higher than 0.2 (1:5), to avoid excessive compression resulting in an altered audio signal. The ratio should not exceed 1 (1:1), a ratio of 1:1 corresponding to no compression.

For the general case in which no distinction is made between a sweeping noise masking contour curve and a sweeping signal tone masking contour curve, the parameters of the compression system are determined such that application of the compression system to the higher one of the signal level of the user masking contour curve at the given frequency 509 and the signal level of the target masking contour curve at the given frequency 509 yields the lower one of the signal level of the user masking contour curve at the given frequency 509 and the signal level of the target masking contour curve at the given frequency 509.

Figure 6:
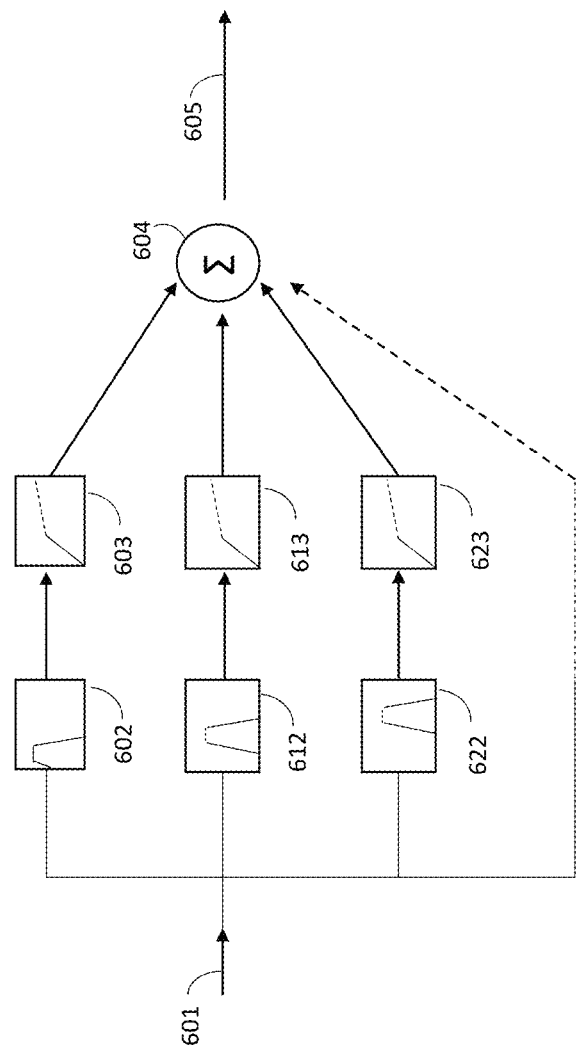
FIG. 6 illustrates an exemplary embodiment of a multi-band compressor circuit.

In FIG. 6 a preferred embodiment of the invention is illustrated. A wide band audio signal is provided at processing input 601 and then spectrally decomposed into a plurality of channels (i.e., frequency bands) by the input band pass filter 602, 612, 622. Each respective channel is provided at a compression input 603, 613, 623. The pathways are then recombined in operator 604 and provided to the processing output 605. For each pathway (i.e., for each channel), the processing of steps 101 to 106 in FIG. 1 is performed.

Figure 7:
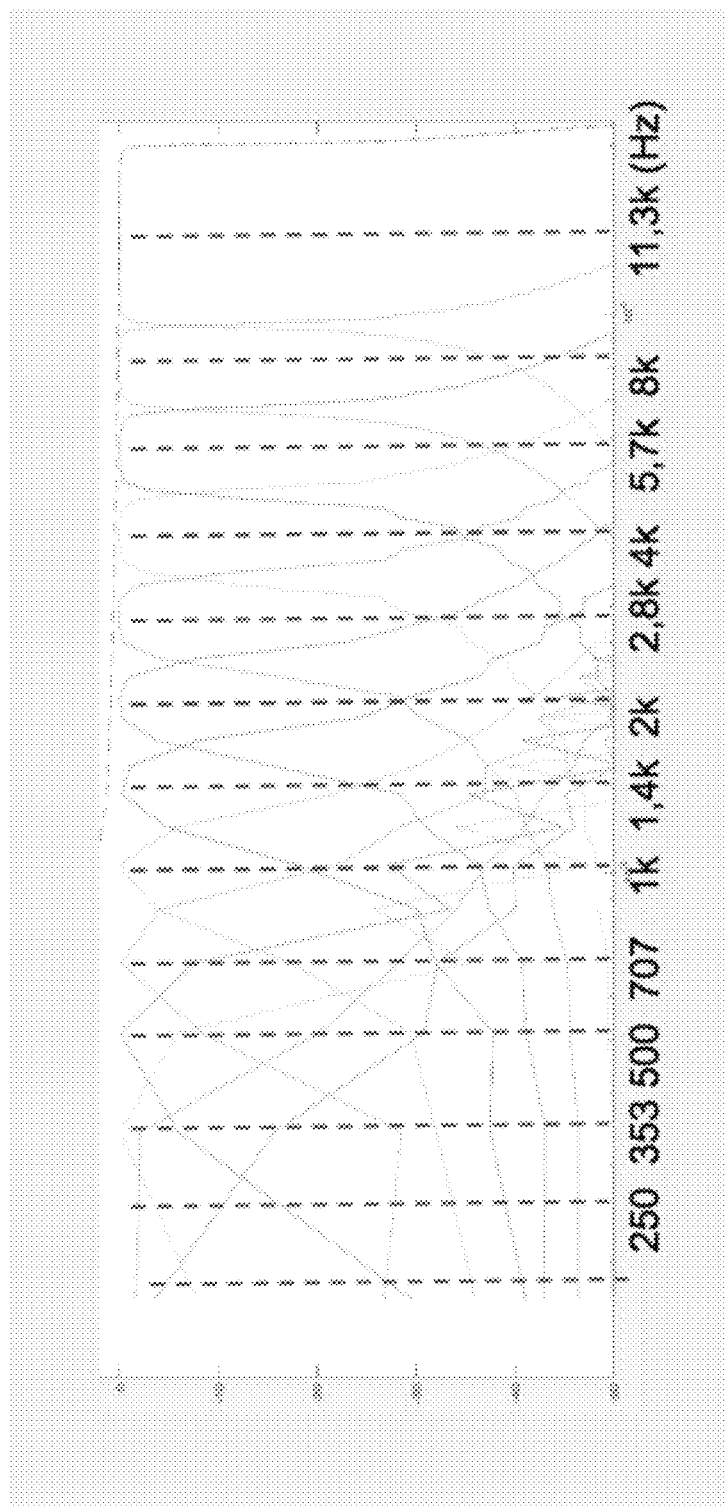
FIG. 7 illustrates the notion of frequency bands.

FIG. 7 illustrates how a portion of the auditory spectrum is divided into frequency bands. The values indicated on the x-axis are the center frequencies of a frequency band. The y-axis is in dB FS. A frequency band may correspond to a DRC channel.

Figure 8:
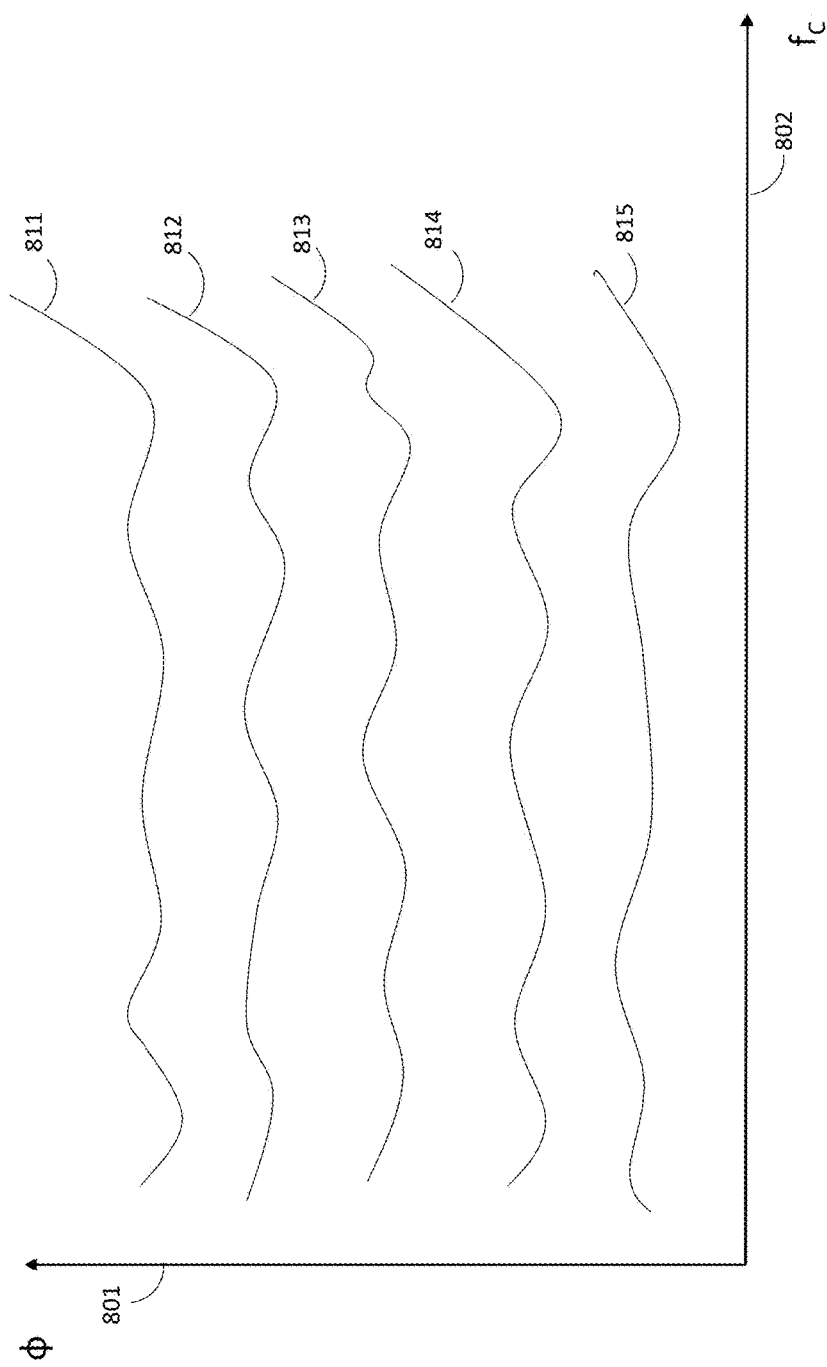
FIG. 8 illustrates how the coefficient of sharpening 4 may be determined.

FIG. 8 illustrates how the coefficient of sharpening Φ may be determined. The relationship between Φ and $f_c$ is not monotonic: the coefficient of sharpening Φ may be a function of both a confidence parameter C and of the frequency of the signal tone, $f_c$. The x-axis 801 represents the frequency of the signal tone $f_c$ and the coefficient of sharpening Φ is represented on the y-axis 802.

The lines 811, 812, 813, 814 and 815 are an assumption of different values of the confidence parameter C. The confidence parameter C may be comprised between 0 and 1, and may be represented for different values, for example the line 811 has a confidence parameter of C=0.2; the line 812 has a confidence parameter of C=0.4; the line 813 has a confidence parameter of C=0.6; the line 814 has a confidence parameter of C=0.8; and the line 814 has a confidence parameter of C=1. The higher the confidence parameter, the more reliable the user masking contour curve is assumed to be. The confidence parameter C may for example be derived for example from metrics such as the number of reversals in a psychometric test, the consistency of someone's response, ambient sound monitoring or monitoring of the background noise, and/or similarity to previous results. The interpolation factor is positively correlated to the confidence parameter For a low confidence parameter, for example for a confidence parameter inferior to 0.5, the coefficient of sharpening will preferably not be too high, i.e. the target masking contour curve will not be too close to the reference masking contour curve, for the reason that too much processing may alter the quality of the outputted sound.

For a high confidence parameter (C higher than 0.8), the target masking contour curve will tend towards the reference masking contour curve. The coefficient of sharpening will also be higher, and hence, more processing will occur.

LIST OF REFERENCE NUMERALS

101 step of obtaining a user's masking contour curve
102 step of determining a target masking contour curve
103 step of comparing a user's masking contour curve with a target masking contour curve
104 step of parameterizing a multi-band compression system
105 step of transferring the obtained parameters to a processor
106 step of processing an output signal to produce an enhanced audio signal
201 quality factor of the target masking contour curve $Q_{10T}$
202 difference between the quality factor of the reference masking contour curve and the quality factor of the user's masking contour curve $\Delta Q_{10}$
203 center frequency $f_c$
204 confidence parameter C
301 user masking contour curve
302 target masking contour curve
303 reference masking contour curve
311 broadness of the user masking contour curve $w_{10U}$
312 broadness of the target masking contour curve $w_{10T}$
313 broadness of the reference masking contour curve $w_{10R}$
401 threshold of the compressor
402 ratio of the compressor
501 frequency (Hz)
502 sound level (dB SPL or HL)
503 sound level input (dB)
504 sound level output (dB)
505 constant tone or noise
506 user masking contour curve
507 target masking contour curve
508 center frequency of the constant tone or noise
509 frequency (arbitrarily chosen)
510 frequency band
511 threshold of the multi-band compression system
512 ratio parameter of the multi-band compression system
521 signal-to-noise ratio of the user masking contour curve
522 signal-to-noise ratio of the target masking contour curve
530 sound level of the target masking contour curve at a given frequency
531 correspondence between the sound level in dB of the target masking curve at a given frequency and the input sound level entering the compression system
541 input sound level entering the compression system
542 sound level outputted by the compression system
601 channel input
602 first band pass filter
612 second band pass filter
622 third band pass filter
603 first dynamic range compressor (DRC)
613 second DRC
623 third DRC
604 operator
605 processing output
801 frequency of the signal tone
802 coefficient of sharpening Φ
811 confidence parameter C=1
812 confidence parameter C=0.8
813 confidence parameter C=0.6
814 confidence parameter C=0.4
815 confidence parameter C=0.2

The invention claimed is:

1. A method of enhancing an audio signal from an audio output device, the method comprising, for a frequency band:
   obtaining, at a multi-band processor, a masking contour curve, covering at least a part of the frequency band;
   deriving a target masking contour curve from the masking contour curve;
   parameterizing a digital compression system based on the sound level of the target masking contour curve at a given frequency and the sound level of the masking contour curve at the same given frequency; and
   outputting the parameters of the digital compression system, wherein the masking contour curve is selected so that its center frequency is not in the same frequency band as the one for which the digital compression system is parameterized.

2. The method according to claim 1, further comprising: processing, using the parameters, an output audio signal to provide an enhanced audio signal.

3. The method according to claim 1, wherein obtaining the masking contour curve involves selecting a masking contour curve from a prestored set of masking contour curves, and wherein the masking contour curve is selected to cover at least part of the frequency band.

4. The method according to claim 1, wherein the masking contour curve is selected so that it extends through the frequency band.

5. The method according to claim 1, wherein the masking contour curve is obtained for frequencies belonging to a human auditory spectrum.

6. The method according to claim 1, wherein the target masking contour curve is derived from the masking contour curve and a reference masking contour curve.

7. The method according to claim 6, wherein the target masking contour curve is obtained by interpolating between the masking contour curve and the reference masking contour curve.

8. The method according to claim 1, wherein the target masking contour curve depends on at least one of the parameters: a center frequency of the masking contour curve and a confidence parameter.

9. The method according to claim 1, wherein the parameters of the digital compression system are determined such that the digital compression system matches the sound levels of the masking contour curve and the target masking contour curve.

10. The method according to claim 1, wherein the parameterizing of the digital compression system comprises setting up of at least two parameters.

11. The method according to claim 10, wherein the at least two parameters comprise threshold and ratio.

12. The method according to claim 1, wherein the method is performed on a plurality of frequency bands.

13. A system for enhancing an audio signal from an audio output device, the system comprising:
a multi-band processor; and
a memory storing instructions, which when executed by the multi-band processor, causes the multi-band processor, for a frequency band, to:
obtain a masking contour curve, covering at least a part of the frequency band;
derive a target masking contour curve from the masking contour curve;
parameterize a digital compression system based on the sound level of the target masking contour curve at a given frequency and the sound level of the masking contour curve at the same given frequency; and
output the parameters of the digital compression system, wherein the masking contour curve is selected so that its center frequency is not in the same frequency band as the one for which the digital compression system is parameterized.

14. The system according to claim 13, wherein obtaining the masking contour curve involves selecting a masking contour curve from a prestored set of masking contour curves, and wherein the masking contour curve is selected to cover at least part of the frequency band.

15. The system according to claim 13, wherein the target masking contour curve is derived from the masking contour curve and a reference masking contour curve.

16. The system according to claim 15, wherein the target masking contour curve is obtained by interpolating between the masking contour curve and the reference masking contour curve.

17. The system according to claim 13, wherein the target masking contour curve depends on at least one of the parameters: a center frequency of the masking contour curve and a confidence parameter.

18. The system according to claim 13, wherein the parameters of the digital compression system are determined such that the digital compression system matches the sound levels of the masking contour curve and the target masking contour curve.

19. The system according to claim 18, wherein the parameters comprise threshold and ratio.

20. The system according to claim 13, wherein the method is performed on a plurality of frequency bands.

21. A non-transitory computer readable medium storing instructions for enhancing an audio signal, which when executed at the multi-band processor, causes the multi-band processor, for a frequency band, to:
obtain a masking contour curve, covering at least a part of the frequency band;
derive a target masking contour curve from the masking contour curve;
parameterize a digital compression system based on the sound level of the target masking contour curve at a given frequency and the sound level of the masking contour curve at the same given frequency; and
output the parameters of the digital compression system, wherein the masking contour curve is selected so that its center frequency is not in the same frequency band as the one for which the digital compression system is parameterized.

22. The non-transitory computer readable medium according to claim 21, wherein obtaining the masking contour curve involves selecting a masking contour curve from a prestored set of masking contour curves, and wherein the masking contour curve is selected to cover at least part of the frequency band.

23. The non-transitory computer readable medium according to claim 21, wherein the target masking contour curve is derived from the masking contour curve and a reference masking contour curve.

24. The non-transitory computer readable medium according to claim 23 wherein the target masking contour curve is obtained by interpolating between the masking contour curve and the reference masking contour curve.

25. The non-transitory computer readable medium according to claim 21, wherein the target masking contour curve depends on at least one of the parameters: a center frequency of the masking contour curve and a confidence parameter.

26. The non-transitory computer readable medium according to claim 21, wherein the parameters of the digital compression system are determined such that the digital compression system matches the sound levels of the masking contour curve and the target masking contour curve.

27. The non-transitory computer readable medium according to claim 26, wherein the at least two parameters comprise threshold and ratio.

28. The non-transitory computer readable medium according to claim 21, wherein the method is performed on a plurality of frequency bands.

* * * * *